(12) United States Patent
Eger

(10) Patent No.: US 9,936,893 B2
(45) Date of Patent: Apr. 10, 2018

(54) DEVICE FOR DETECTING ELECTRIC POTENTIALS

(71) Applicant: Drägerwerk AG & Co. KGaA, Lübeck (DE)

(72) Inventor: Marcus Eger, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 231 days.

(21) Appl. No.: 14/923,914

(22) Filed: Oct. 27, 2015

(65) Prior Publication Data

US 2016/0113547 A1    Apr. 28, 2016

(30) Foreign Application Priority Data

Oct. 28, 2014    (DE) .................. 10 2014 015 895

(51) Int. Cl.
*A61B 5/053* (2006.01)
*A61B 5/00* (2006.01)
(Continued)

(52) U.S. Cl.
CPC ........ *A61B 5/0531* (2013.01); *A61B 5/04004* (2013.01); *A61B 5/6801* (2013.01); *G06G 7/14* (2013.01)

(58) Field of Classification Search
CPC . A61B 5/0042; A61B 5/04004; A61B 5/0408; A61B 5/053; A61B 5/0531;
(Continued)

(56) References Cited

U.S. PATENT DOCUMENTS

| 4,200,109 A | * | 4/1980 | McMorrow, Jr. .... | A61B 5/0424 128/908 |
| 4,890,630 A | * | 1/1990 | Kroll .................... | A61B 5/0428 128/902 |

(Continued)

FOREIGN PATENT DOCUMENTS

| CN | 1251643 C | 4/2006 |
| DE | 29 26 165 A1 | 1/1980 |

(Continued)

OTHER PUBLICATIONS

Chinese Search Report for CN Patent Application No. 2015110359316.*

(Continued)

*Primary Examiner* — David J McCrosky
(74) *Attorney, Agent, or Firm* — McGlew and Tuttle, P.C.

(57) ABSTRACT

A device for detecting electric potentials includes a plurality of measuring inputs (9) for connecting to measuring electrodes (11), which can be placed on the body of a patient (3), a plurality of measuring amplifiers ($Op_1, \ldots, Op_N$), and a potential output (27) for connecting to an additional electrode (31), which can be placed on the body of the patient (3), to which a preset voltage can be applied. A summing unit (17) sends a signal, which is an indicator of the mean value of the signals sent by the measuring amplifiers (Op1, . . . , OpN). A current-measuring device (29) sends a current signal, which is proportional to the current flowing through the potential output. An analyzing unit (35) is connected to receive a potential output voltage signal, the summing unit output (19) signal and the current-measuring device signal. The analyzing unit is configured to generate an impedance signal from the fed signals.

9 Claims, 2 Drawing Sheets

(51) Int. Cl.
*G06G 7/14* (2006.01)
*A61B 5/04* (2006.01)

(58) Field of Classification Search
CPC ... A61B 5/0536; A61B 5/4064; A61B 5/7203; A61B 5/7225; A61B 5/7292; G06G 7/14
USPC ............ 600/544–547; 623/25; 702/104
See application file for complete search history.

(56) References Cited

U.S. PATENT DOCUMENTS

| | | | |
|---|---|---|---|
| 6,487,449 B1* | 11/2002 | Kaiser | A61B 5/0424 600/547 |
| 9,232,902 B2* | 1/2016 | Takahashi | A61B 5/0408 |
| 2002/0183797 A1 | 12/2002 | Kaiser et al. | |
| 2011/0251817 A1* | 10/2011 | Burns | A61B 5/0531 702/104 |
| 2014/0247058 A1* | 9/2014 | Mortara | A61B 5/0531 324/601 |
| 2014/0257119 A1* | 9/2014 | LeMay | A61B 5/6844 600/509 |
| 2015/0241505 A1* | 8/2015 | Freeman | A61B 5/0402 324/538 |
| 2016/0029915 A1* | 2/2016 | Peterson | A61B 5/0424 600/509 |

FOREIGN PATENT DOCUMENTS

| | | |
|---|---|---|
| JP | 2014124438 A | 7/2014 |
| WO | 2012056882 A1 | 5/2012 |
| WO | 2014021883 A1 | 2/2014 |

OTHER PUBLICATIONS

Bruce B. Winter et al., Driven-Right-Leg Circuit Design, IEEE Transactions on Biomedical Engineering, vol. BME-30, No. 1, Jan. 1983.

* cited by examiner

DEVICE FOR DETECTING ELECTRIC POTENTIALS

CROSS REFERENCE TO RELATED APPLICATIONS

This application claims the benefit of priority under 35 U.S.C. § 119 of German Patent Application DE 10 2014 015 895.0 filed Oct. 28, 2014, the entire contents of which are incorporated herein by reference.

FIELD OF THE INVENTION

The present invention pertains to a device for detecting electric potentials with a plurality of measuring inputs for connecting to measuring electrodes which can be placed on the body of a patient, with a plurality of measuring amplifiers, wherein one of the plurality of measuring amplifiers is associated with each measuring input and each measuring input is connected to an input of the measuring amplifier associated with this, with a potential output for connection to an additional electrode, which can be placed on the body of a patient, wherein the potential output is designed such that a preset voltage can be applied to it, with a summing unit, which is connected to the outputs of the measuring amplifiers and which is designed to send a signal, which is an indicator of the mean value of the signals sent by the measuring amplifiers, as well as a method for determining the impedance of the connection between the additional electrode and the skin of a patient.

BACKGROUND OF THE INVENTION

Measured electric potentials, for example, on the skin of a patient and the useful signal contained in these potentials lies only in the mV range, as may be the case, for example, in an electrocardiogram (ECG) or an electromyogram (EMG), the following problems arise.

Since the body of the patient is surrounded by electric fields, potentials are formed due to capacitive coupling on the skin of the patient. This effect can generally be described in such a way that the body is coupled capacitively especially to a 230V/50 Hz alternating voltage field (it would be 60 Hz in the USA) which is caused by power supply sources located in the surrounding area of the patient. For the sake of safety, it is, however, not allowable to couple the patient himself to a uniform surrounding ground, because this would cause a considerable risk to the patient.

In addition, likewise for the sake of safety, a measuring device, to which the electrodes on the skin of the patient are connected, must also be galvanically separated from a surrounding ground. This in turn implies that the measuring device is also coupled with its internal ground capacitively to the surrounding area, so that the problem arises that the device ground lies on a potential, whose level is not known, and which generally differs from the potential of the patient.

In order to now at least achieve that the patient and the ground of the measuring device lie on the same potential or at least a fixed potential difference is present between both, it is known to connect the device ground and the body of the patient to one another via an additional electrode.

Since, however, the device ground and the patient may generally lie on a different potential because of the inhomogeneity of the surrounding fields, which arises from the different capacitive coupling to the surrounding area, an equalizing current flows, which leads to a so-called common mode signal because of the impedance of the coupling to the patient via the additional electrode, which is amplified by the amplifiers in the measuring device. When the useful signals actually to be detected with the measurement are very small, the common mode signal leads to the actual useful signal no longer being able to be resolved. Moreover, the difficulty arises that the amplifiers must have a high input dynamic range, so that the useful signal and the higher common mode signal overlaying this can be processed. Furthermore, a digital electronic analyzing unit arranged downstream has to provide a high number of bits per measured value to be able to process the large signals.

For this purpose, it is known from Bruce B. Winter et al., Driven-Right-Leg Circuit Design, IEEE Transactions on Biomedical Engineering, Vol. BME-30, No. 1, January 1983, to apply a potential, which corresponds to the mean value of the signals detected at the measuring electrodes, wherein this mean value signal is also amplified in inverted form, i.e., a negative back coupling is present, to the additional, so-called common or additional electrode arranged on the patient by the measuring device.

It has now been shown that the quality of the signals detected at the measuring electrodes depends highly on how well the contact is between the additional electrode and the skin of the patient. Already when the electrode is easily detached from the skin of the patient, a markedly increased noise occurs in the measured signals or these signals are frequently unusable. Especially when a potential difference is present between the patient and the measuring device and an equalizing current flows over the additional electrode, there is a drop in voltage at the additional electrode/skin contact, which depends on the contact impedance. The quality of the measured signals thus depends highly on the contact impedance between the additional or common electrode and the patient.

SUMMARY OF THE INVENTION

Based upon this, an object of the present invention is to provide a device for detecting potentials, which makes it possible to determine the contact impedance between the additional electrode and the patient in a reliable manner.

This object is accomplished by the potential output being connected to a current-measuring device, which is designed to send a current signal, which is proportional to the current flowing through the potential output, by an analyzing unit being provided, which is connected such that a signal corresponding to the signal at the potential output, the signal sent by the summing unit to its output and the signal sent by the current-measuring device are fed to it, and by the analyzing unit being designed to generate an impedance signal from the fed signals.

The means for accomplishing the object according to the present invention is based on the idea that the mean value of the potentials detected at the measuring electrodes on the patient corresponds directly to the common mode signal or the common mode voltage. On the other hand, the overall voltage dropping between the patient and the potential output, which likewise corresponds to the common mode voltage, is composed of the voltage drop at the additional electrode, which is determined by the questionable contact impedance, as well as the voltage drop over a measuring resistor and optionally an additional voltage, which is additionally applied to the potential output.

As a whole, the possibly present additional voltage as well as the voltage dropped at the measuring resistor are thus applied to the potential output. When the current flowing through the potential output is now additionally determined, it is possible to calculate the impedance at the additional electrode by means of the analyzing unit from the mean value signal generated by means of the summing unit and from the current signal, wherein the additional voltage, which is additionally applied to the potential output, still possibly comes into consideration. For example, the current signal and the mean value signal may undergo a Fourier transformation and the quotients of the Fourier coefficients may be formed. However, other possibilities of generating an impedance signal are also conceivable.

In this way, it is simply possible to continuously monitor the impedance at the additional electrode by measuring the current through the potential output as well as by determining the mean value signal. In particular, an upper limit for the impedance can be monitored, or the signal generated by the analyzing unit can be used for generating an alarm, when a fast change, for example, an increase, in the impedance occurs, which is caused by the separation of the additional electrode from the skin of the patient.

In a preferred exemplary embodiment of the present invention, the mean value signal generated by the summing unit is used to apply it to the potential output. In a further preferred manner, the output of the summing unit is connected in this case to the input of a first amplifier (further amplifier), wherein the output of the first amplifier is connected to the potential output.

In this process, the so-called Driven-Right-Leg principle is implemented, according to which a signal, which is proportional to the mean value of the signals detected at the measuring electrodes, is applied to an additional electrode on the body of the patient. Consequently, the common mode signal, which is contained in the potentials detected by the measuring amplifiers, can be further reduced. This optionally amplified and inverted mean value signal is then an additional voltage, which must be taken into consideration in the determination of the contact impedance by the analyzing unit, which is why this corresponding signal must likewise be fed to the analyzing unit.

Moreover, the current-measuring device is then arranged in such a way that it is connected between the output of the first amplifier and the potential output, wherein the first amplifier amplifies the mean value signal by the summing unit in a suitable manner.

In addition, in another preferred embodiment, the output signal of the summing unit can be fed to second inputs of the measuring amplifiers, so that, in addition or as an alternative to the Driven-Right-Leg principle, the reference amplifier principle is also implemented, in which a signal which is proportional to the common mode signal at the amplifiers is subtracted from the measurement signals. Thus, the mean value signal may also be used to additionally reduce the effect of the common mode signal at the output of the respective measuring amplifier.

According to a second aspect of the present invention, the above object is accomplished by a method for determining the impedance of the connection between an additional electrode and the skin of a patient with a device, having a plurality of measuring inputs for connecting to measuring electrodes, which can be placed on the body of a patient, a plurality of measuring amplifiers, wherein one of the plurality of measuring amplifiers is associated with each measuring input and each measuring input is connected to an input of the measuring amplifier associated with this, a potential output for connecting to the additional electrode, wherein the potential output is designed such that a preset voltage can be applied to it, wherein the method has the following steps:

generating a mean value signal, which is an indicator of a mean value of the level of the signals sent by the measuring amplifiers, applying a preset voltage to the potential output and providing a voltage signal, which is an indicator of the level of the voltage, which is applied to the potential output, detecting the current flowing through the potential output and generating a current signal, which is an indicator of the level of the current flowing through the potential output, and generating an impedance signal from the mean value signal and the current signal.

The advantages already explained in connection with the device according to the present invention apply to this method.

Besides feeding the mean value signal, optionally in an amplified form, to the additional electrode and/or to the second inputs of the measuring amplifiers in preferred embodiments, it is also possible that a voltage varying over time, for example, a sinus-shaped voltage variation, is applied as additional voltage to the potential output. Such a variation is then likewise taken into account in the determination of the impedance signal.

The present invention is explained below based on a drawing showing only preferred exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
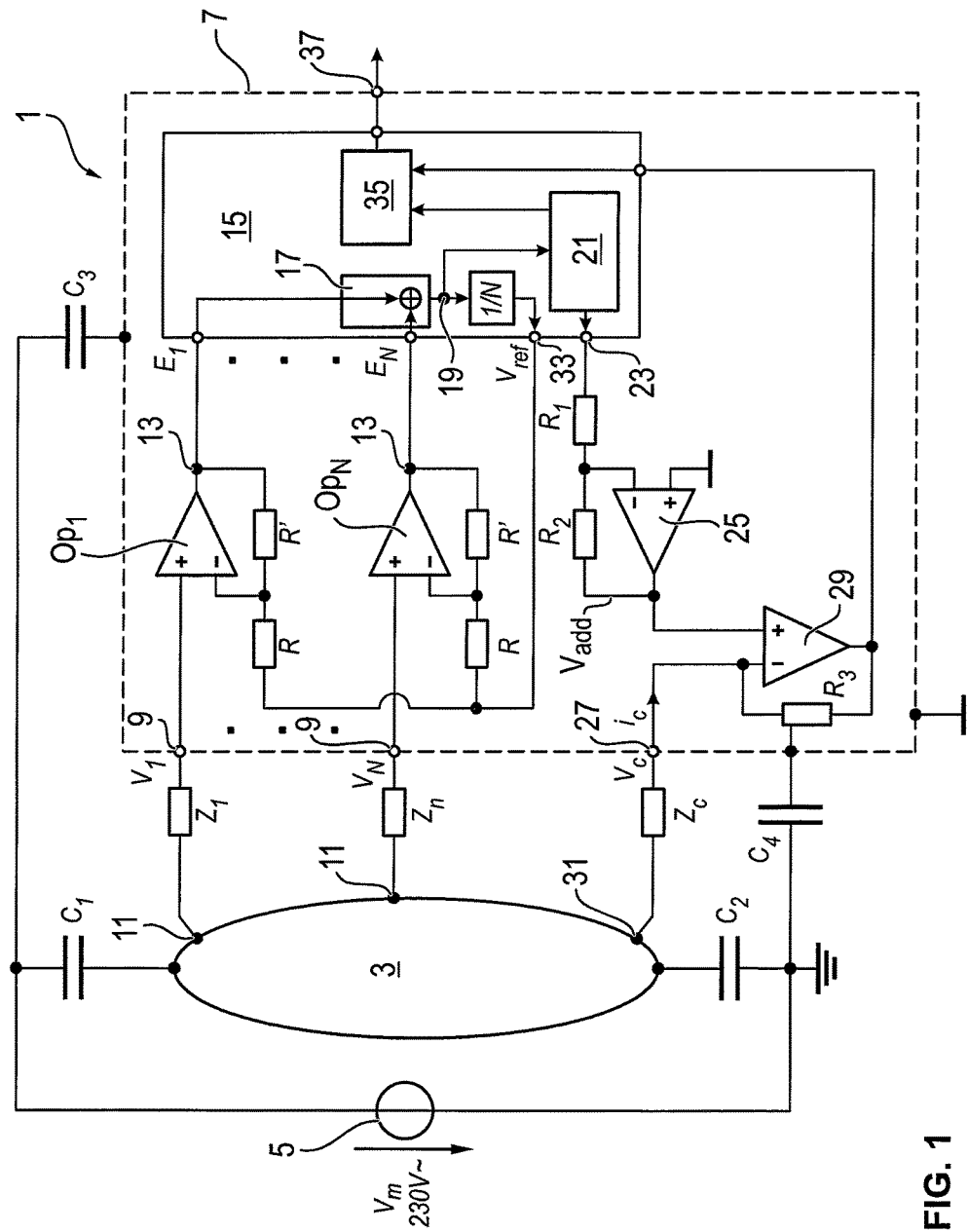
FIG. 1 is a schematic view of a first exemplary embodiment of a device according to the present invention.

Referring to the drawings, FIG. 1 shows the first exemplary embodiment of a device 1 according to the present invention, wherein the device 1 is connected to a patient 3. The capacities $C_1$, $C_2$, $C_3$ and $C_4$ as well as the power supply 5 suggest in this connection that both the patient 3 and the housing 7 of the device 1 are coupled capacitively to the surrounding area and especially to a 50 Hz or 60 Hz alternate voltage field, so that the patient 3 and the housing 7, which forms the device ground of the device 1, lie on potentials that are undetermined and different from one another.

The device 1 according to the present invention has a plurality of measuring inputs 9, via which the device can be connected to electrodes 11 on the patient 3, so that a potential on the skin of the patient 3 can be measured via the electrodes 11. The impedances $Z_1$, $Z_N$ suggest in this connection that the coupling between the electrodes 11 and the skin of the patient 3 is connected to an impedance. However, the present invention is not limited to the use in electrodes, which are placed on the skin of a patient, but rather may also be used, for example, in invasively applied electrodes.

Furthermore, the device 1 has measuring amplifiers $Op_1, \ldots, Op_N$, which have a first, non-inverting input characterized by "+" and a second, inverting input characterized by "−". In the exemplary embodiment described here, the measuring amplifiers $Op_1, \ldots, Op_N$ are connected as non-inverting amplifiers in reference to the input signals $V_1, \ldots, V_N$ by the measuring inputs 9. However, they may also be connected as inverting amplifiers, wherein this must then, however, be taken into consideration in the further processing of the output signals $E_1, \ldots, E_N$ of the measuring amplifiers $Op_1, \ldots, Op_N$.

The outputs 13 of the measuring amplifiers $Op_1, \ldots, Op_N$ are connected to a microprocessor unit 15, which is designed by program implementation such that the following functions or units are implemented by it.

While the units explained below in the preferred exemplary embodiment described here are implemented by a digitally working microprocessor unit, it is just as possible for these units or functions to be implemented by analog technique, for example, to implement them by means of operational amplifiers. This is likewise covered by the scope of the present invention.

First, a summing unit 17 is implemented by the microprocessor unit 15, which is configured such that the microprocessor unit 15 is connected to the outputs 13 of the measuring amplifiers $Op_1, \ldots, O_N$, and is likewise coupled to these outputs 13. The microprocessor unit 15 sends a signal to an output 19, which corresponds to the mean value of the output signals $E_1, \ldots, E_N$ sent by the measuring amplifiers $Op_1, \ldots, Op_N$ in this exemplary embodiment, i.e., the signal is either equal to the mean value or proportional to the mean value.

Furthermore, the microprocessor unit 15 is designed such that the mean value signal, which is generated at the output 19 of the summing unit 17, is fed to an output 23 via a detection unit 21. The output 23 is connected to a potential output 27 of the device 1 via a first amplifier (further amplifier) 25.

Between the output of the first amplifier 25 and the potential output 27, the device 1 has another, second amplifier (another amplifier) 29 in the preferred exemplary embodiment described here, which is connected as a current-voltage converter, so that a signal is generated at its output, which signal corresponds to the current between the output of the first amplifier 25 and the potential output 27. Thus, the second amplifier 29 works as a current-measuring device, and the output signal thereof is fed to the microprocessor unit 15.

The potential output 27 of the device 1 is connected to a common or additional electrode 31, which is likewise placed on the skin of the patient 3, wherein the contact between the additional electrode 31 and the skin of the patient 3 has an impedance $Z_C$, which shall be monitored as continuously as possible in order to detect when, for example, the additional electrode 31 is detached from the skin of the patient 3.

Moreover, the mean value signal is sent via another output 33 by the microprocessor unit 15 and is fed from there to the second, inverting inputs of the measuring amplifiers $Op_1, \ldots, O_N$ characterized by "−" (minus sign). Thus, the reference amplifier principle known from the state of the art is implemented by this feeding back of the mean value signal.

Finally, an analyzing unit, which is connected, on the one hand, to the detection unit 21 and, on the other hand, to the output of the second amplifier 29, is implemented in the microprocessor unit 15. Thus, the starting signal of the summing unit 17, a signal, which corresponds to the voltage, which is applied to the potential output 27, and by the first amplifier 25, as well as a current signal, which corresponds to the current flowing through the potential output 27, are fed to the analyzing unit 35.

On the basis of these signals, the analyzing unit calculates an impedance signal from the mean value signal and the current signal. This impedance signal may be sent to an output 37 of the device 1 and be further used, for example, for generating an alarm. The impedance signal may be generated such that the current signal and the mean value signal undergo Fourier transformation and the quotients of the Fourier coefficients are determined.

Figure 2:
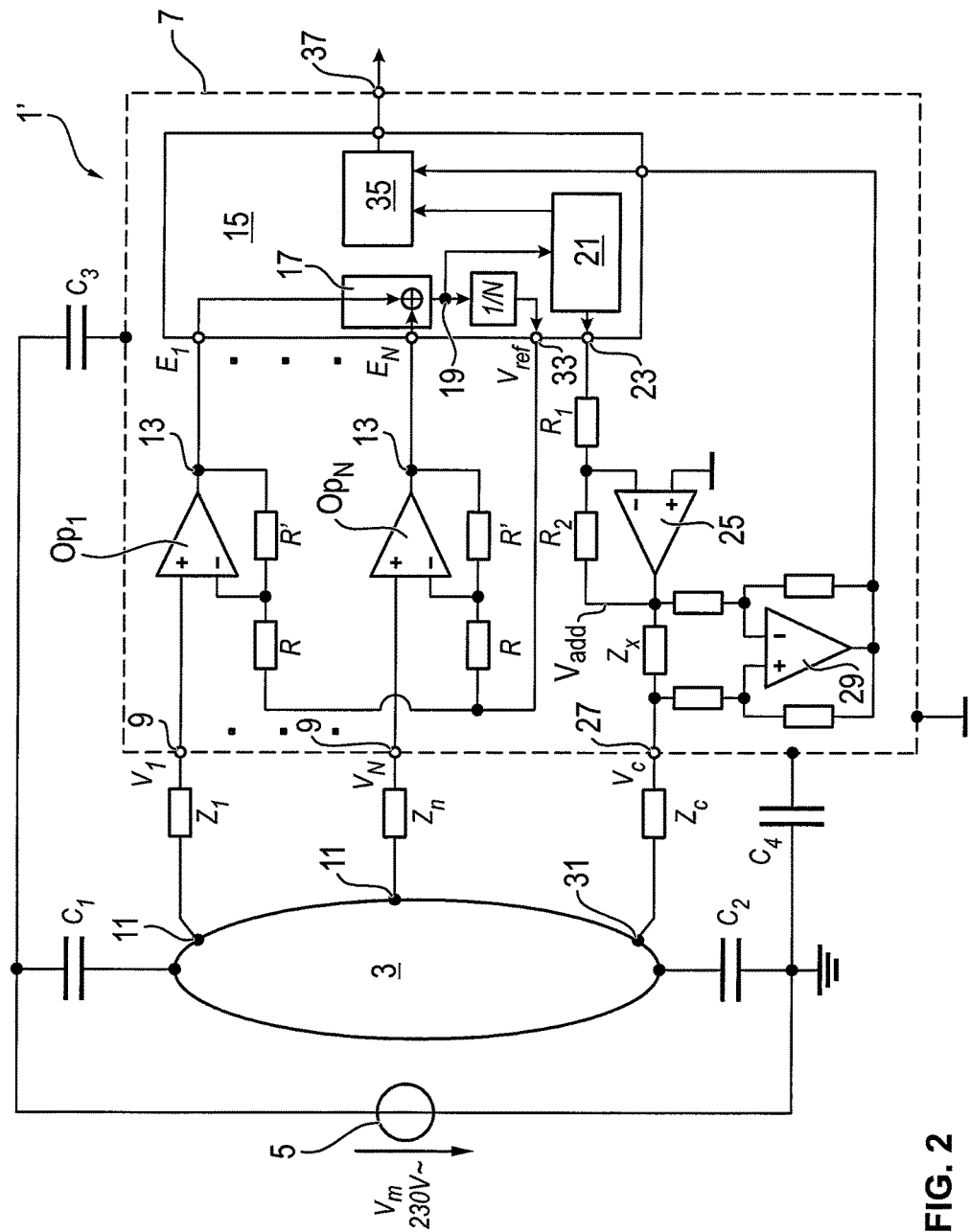
FIG. 2 is a schematic view of a second exemplary embodiment.

The second exemplary embodiment of a device according to the present invention, shown in FIG. 2, differs from the exemplary embodiment from FIG. 1 only in that the second amplifier 29 in this case is connected together with a measuring resistor $Z_X$, such that this detects the voltage drop via the measuring resistor $Z_X$ and consequently detects the current through the potential output. Thus, the combination of a second amplifier 29 and measuring resistor $Z_X$ is herewith used as a current-measuring device. Otherwise, the device 1' works analogously to that of FIG. 1.

The following is utilized in both exemplary embodiments. Based on FIG. 2, the equation $$V_{CM} = V_C + V_X + V_{add}$$

is obtained for the common mode voltage $V_{CM}$ and the common mode signal.

$V_C$ is the voltage dropping between the potential output 27 and the patient, for which $$V_C = Z_C \cdot I_C$$

wherein $I_C$ is the current flowing through the potential output 27 and $Z_C$ is the questionable contact impedance. $V_X$ is the voltage dropped at a measuring resistor $Z_X$ for which the equation $$V_X = Z_X \cdot I_C$$

likewise applies. $V_{add}$ is an additional voltage, which can be applied to the potential output 27. However, in principle, this voltage may also be zero, i.e., $V_{add} = 0$.

When one combines the first two equations, on the one hand, and utilizes the relationship, the mean value $\overline{E_I}$ of the starting signals $E_1, \ldots, E_N$ corresponds to the common mode voltage, i.e., $\overline{E_I} = V_{CM}$, $$Z_C = \frac{\overline{E_I} - V_X - V_{add}}{I_C}$$

is obtained.

In the exemplary embodiments, $I_C$ is detected by means of the current-measuring device, i.e., the second amplifier 29, either directly or as voltage at the measuring resistor $Z_X$, and a corresponding signal is fed to the analyzing unit 35. Moreover, $\overline{E_I}$ or a signal that is proportional to it is determined by the summing unit 17 and a corresponding signal is likewise fed to the analyzing unit 35. Finally, a signal corresponding to $V_{add}$ is sent by the detection unit 21 to the analyzing unit 35, so that based on the last equation of the analyzing unit 35, an impedance signal is generated and can be sent to the output 37.

The result of the last equation in this connection is that the level of this signal is in any case proportional to the quotient of the mean value signal $\overline{E_I}$ and the current $I_C$ through the potential output 27, wherein depending on how $V_{add}$ is selected, this ratio, for example, corresponding to the amplification in the first amplifier 29, must be corrected.

It has been assumed up to now that the additional voltage $V_{add}$ is a voltage that is proportional to the mean value signal $\overline{E}_l$. However, the detection unit 21 may generate an additional voltage signal $V_{add}$, which has a known, variable course over time, for example, a sinus-shaped course. Corresponding information is then sent from the detection unit 21 to the information from the analyzing unit 35, so that a corresponding impedance signal may then also be calculated, wherein the above last equation is used here as well.

While specific embodiments of the invention have been shown and described in detail to illustrate the application of the principles of the invention, it will be understood that the invention may be embodied otherwise without departing from such principles.

APPENDIX

List of Reference Numbers 1, 1' Device
3 Patient
5 Power supply
7 Housing
9 Measuring input
11 Electrode
13 Output—Measuring amplifier
15 Microprocessor unit
17 Summing unit
19 Output—summing unit
21 Detection unit
23 Output—microprocessor unit
25 First amplifier
27 Potential output
29 Second amplifier
31 Additional electrode
33 Additional output
35 Analyzing unit
37 Output
$V_i$ Input signal
$E_i$ Output signal
$Op_i$ Measuring amplifier

What is claimed is:

1. A device for detecting electric potentials, the device comprising:
a plurality of measuring inputs for connecting to measuring electrodes, the measuring electrodes being adapted to be placed on the body of a patient;
a plurality of measuring amplifiers, each of the plurality of measuring amplifiers being associated with a respective one of the measuring inputs and each of the measuring inputs being connected to an input of the associated measuring amplifier;
a potential output for connecting to an additional electrode, which can be placed on the body of the patient, the potential output being designed such that a preset voltage can be applied thereto;
a summing unit connected to the outputs of the measuring amplifiers, the summing unit being configured to send a signal, which is an indicator of the mean value of the signals sent by the measuring amplifiers;
a current-measuring device connected to the potential output, the current-measuring device being configured to send a current signal, which is proportional to the current flowing through the potential output; and
an analyzing unit connected to receive a signal corresponding to the voltage at the potential output, the signal sent by the summing unit at the output thereof and the signal sent by the current-measuring device, the analyzing unit being configured to generate an impedance signal from the received signals.

2. A device in accordance with claim 1, wherein the output of the summing unit is connected to the potential output.

3. A device in accordance with claim 2, further comprising a further amplifier is provided, wherein
the output of the summing unit is connected to an input of the further amplifier;
an output of the further amplifier is connected to the potential output; and
the current-measuring device is operatively connected between the output of the further amplifier and the potential output.

4. A device in accordance with claim 1, wherein:
the measuring amplifiers have a first and a second input;
each measuring input is connected to the first input of the associated measuring amplifier; and
the output of the summing unit is connected to the second inputs of the measuring amplifiers.

5. A method for determining the impedance of the connection between an additional electrode and the skin of a patient, the method comprising the steps of:
providing a device comprising a plurality of measuring inputs for connecting to measuring electrodes, the measuring electrodes being adapted to be placed on the body of a patient, a plurality of measuring amplifiers, wherein one of the plurality of measuring amplifiers is associated with each measuring input and each measuring input is connected to an input of the associated measuring amplifier, and a potential output for connecting to the additional electrode, wherein the potential output is designed such that a preset voltage can be applied thereto;
generating a mean value signal, which is an indicator of a mean value of the level of the signals sent by the measuring amplifiers;
applying a preset voltage to the potential output;
providing a voltage signal, which is an indicator of the level of the voltage, which is applied to the potential output;
detecting current flowing through the potential output;
generating a current signal, which is an indicator of the level of the current flowing through the potential output; and
generating an impedance signal from the mean value signal and the current signal.

6. A method in accordance with claim 5, wherein the mean value signal is applied to the potential output.

7. A method in accordance with claim 6, wherein the mean value signal is amplified, and the amplified signal is fed to the potential output.

8. A method in accordance with claim 5, wherein:
the measuring amplifiers have a first input and a second input;
each measuring input is connected to a first input of the associated measuring amplifier associated; and
the mean value signal is fed to the second inputs of the measuring amplifiers.

9. A method for determining an impedance of a connection between an additional electrode and skin of a patient, the method comprising the steps of:
providing a device comprising a plurality of measuring inputs for connecting to measuring electrodes, said measuring inputs receiving electrical signals of the patient from the measuring electrodes, said device including a plurality of measuring amplifiers, each of said measuring amplifiers receiving the electrical signals from one of said measuring inputs and generating an output electrical signal proportional to the received electrical signal, wherein one of said plurality of measuring amplifiers is associated with each said measuring input and each said measuring input is connected to an input of said associated measuring amplifier, said device including a potential output configure to connect to, and apply a voltage to, the additional electrode;

generating a mean value signal which is a mean value of the output signals generated by said measuring amplifiers;

applying the voltage to said potential output;

providing a voltage signal, which is an indicator of a value of the voltage which is applied to said potential output;

detecting current flowing through said potential output;

generating a current signal which is an indicator of the magnitude of the current flowing through said potential output; and generating an impedance signal from the mean value signal and the current signal.

* * * * *